United States Patent
Van Egmond et al.

(10) Patent No.: US 7,141,711 B2
(45) Date of Patent: *Nov. 28, 2006

(54) CATALYST FINES HANDLING PROCESS

(75) Inventors: Cor F. Van Egmond, Pasadena, TX (US); Richard E. Walter, Long Valley, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 512 days.

This patent is subject to a terminal disclaimer.

(21) Appl. No.: 10/395,380

(22) Filed: Mar. 24, 2003

(65) Prior Publication Data

US 2004/0192992 A1 Sep. 30, 2004

(51) Int. Cl.
*C07C 1/00* (2006.01)
(52) U.S. Cl. ............. 585/640; 585/950; 208/176
(58) Field of Classification Search ............. 585/638, 585/639, 640, 950; 208/176
See application file for complete search history.

(56) References Cited

U.S. PATENT DOCUMENTS

| | | | |
|---|---|---|---|
| 4,935,568 A | 6/1990 | Harandi et al. | 585/300 |
| 5,264,645 A | 11/1993 | Hugues et al. | 585/640 |
| 5,744,680 A * | 4/1998 | Mulvaney et al. | 585/640 |
| 6,121,504 A | 9/2000 | Kuechler et al. | 585/640 |
| 6,137,022 A * | 10/2000 | Kuechler et al. | 585/638 |
| 6,403,854 B1 * | 6/2002 | Miller et al. | 585/638 |
| 6,482,998 B1 | 11/2002 | Kuechler et al. | 585/638 |
| 6,777,585 B1 * | 8/2004 | Van Egmond | 585/638 |

FOREIGN PATENT DOCUMENTS

| | | |
|---|---|---|
| GB | 808 327 | 2/1959 |
| WO | WO 03/037834 | 5/2003 |

* cited by examiner

*Primary Examiner*—Glenn Caldarola
*Assistant Examiner*—In Suk Bullock

(57) ABSTRACT

The present invention is a process for removing catalyst fines from a reactor effluent stream that has catalyst fines therein. The process comprises withdrawing the reactor effluent stream from the reactor. The reactor effluent stream is transported in a first conduit to a quench device and is quenched to form a quenched effluent stream and a liquid fraction containing a majority of the catalyst fines. The liquid fraction is transported in a second conduit to a solids separation device. The conditions under which the catalyst fines are moved prevent accumulation of catalyst fines in the catalyst fines process steps.

52 Claims, 1 Drawing Sheet

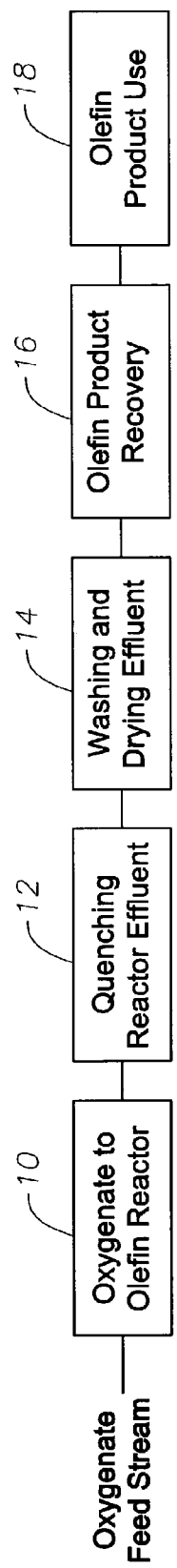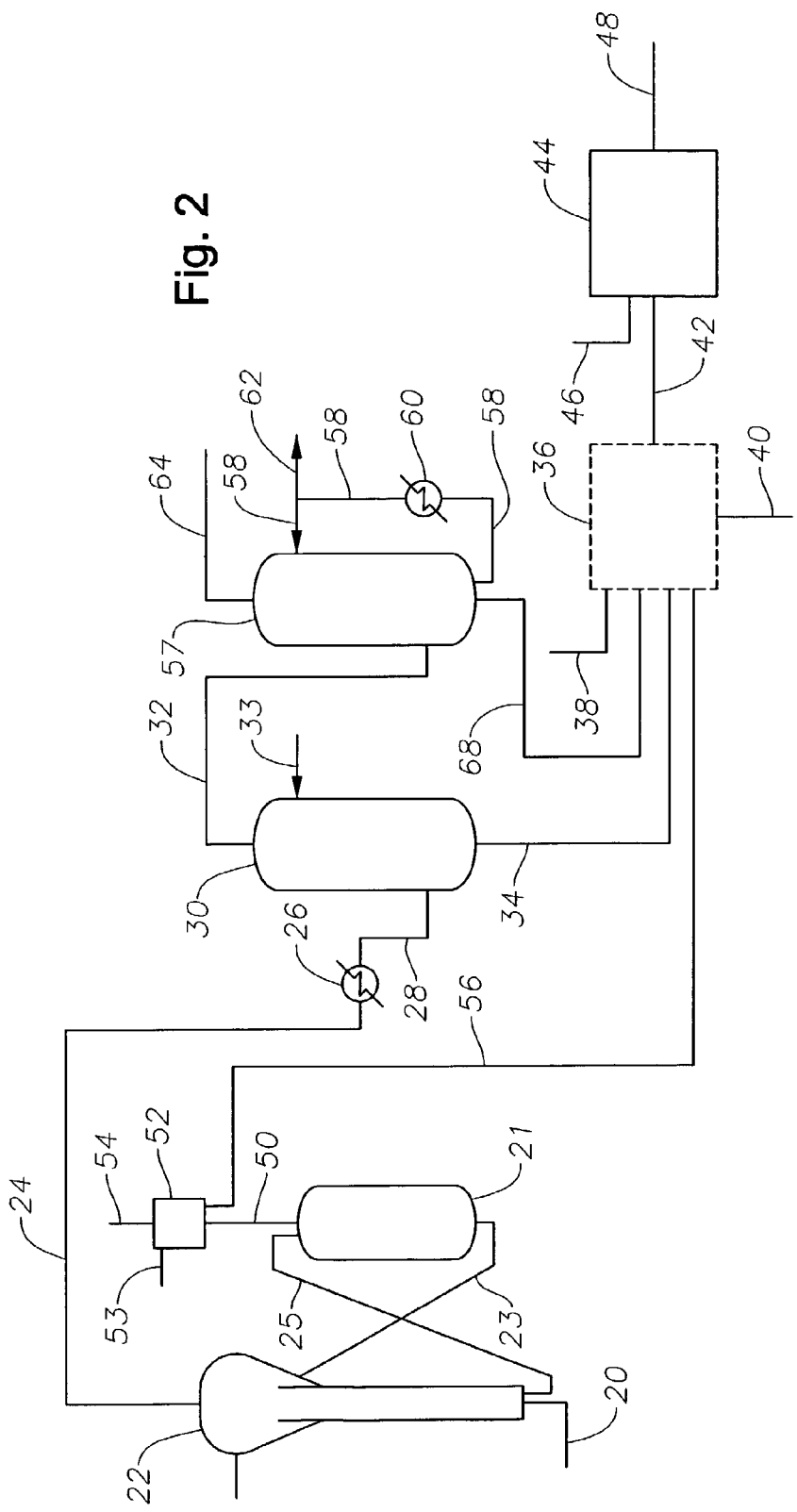

CATALYST FINES HANDLING PROCESS

FIELD OF THE INVENTION

The present invention relates to handling and disposal of catalyst fines in a process for converting methanol to an olefin product.

BACKGROUND OF THE INVENTION

Olefins are traditionally produced from petroleum feedstock by catalytic or steam cracking processes. These cracking processes, especially steam cracking, produce light olefins such as ethylene and/or propylene from a variety of hydrocarbon feedstock. Ethylene and propylene are important commodity petrochemicals useful in many processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefins. This process is referred to as the oxygenate-to-olefin process. The preferred oxygenate for light olefin production is methanol. The process of converting methanol-to-olefins is called the methanol-to-olefins process.

There are numerous technologies available for producing oxygenates, and particularly methanol, including fermentation or reaction of synthesis gas derived from natural gas, petroleum liquids, carbonaceous materials including coal, recycled plastics, municipal waste or any other organic material. The most common process for producing methanol is a two-step process of converting natural gas to synthesis gas. Then, synthesis gas is converted to methanol.

Generally, the production of synthesis gas involves a combustion reaction of natural gas, mostly methane, and an oxygen source into hydrogen, carbon monoxide and/or carbon dioxide. Synthesis gas production processes are well known, and include conventional steam reforming, autothermal reforming or a combination thereof.

Synthesis gas is then processed into methanol. Specifically, the components of synthesis gas (i.e., hydrogen, carbon monoxide and/or carbon dioxide) are catalytically reacted in a methanol reactor in the presence of a heterogeneous catalyst. For example, in one process, methanol is produced using a copper/zinc oxide catalyst in a water-cooled tubular methanol reactor.

The methanol is then converted to olefins in a methanol-to-olefins process. The methanol-to-olefins reaction is highly exothermic and has a large amount of water. Water comprises as much as one half of the total weight of the output stream of the reactor or effluent stream. Consequently, the water must be removed by condensation in a quench device to isolate the olefin product. A quench device cools the effluent stream to the condensation temperature of water. Quenching the product recovers large quantity of water at the temperature near the boiling point of the quench medium.

Oxygenate-to-olefins reactions, including methanol-to-olefin reactions, use a catalyst, preferably a molecular sieve catalyst. Catalyst particles are circulated through the reactor system and are retained by the particle size separators or cyclones. The catalyst particles break down into smaller particles as they make physical contact with the hardware of the reactor system and pass through the particle size separators or cyclones into the effluent stream. As used herein, any catalyst particles that are found in the effluent stream are referred to as catalyst fines. After passing through the cyclones, catalyst fines are carried along in the effluent stream. Typically, the particle size separators retain catalyst particles that are above 40 microns in size. Catalyst particles are removed from the effluent stream in a quench device, and typically are suspended in a bottoms stream of the quench device. The presence of catalyst fine in the effluent stream or the bottoms stream of a quench device presents two unique problems. First, the catalyst fines can erode the walls of the vessel as they travel through the reactor. Second, catalyst fines can settle or collect in parts of the equipment. This settling or accumulation can damage equipment, cause inefficient operation, shut downs and frequent cleaning.

U.S. Pat. No. 6,121,504 describes a quench apparatus for an oxygenate-to-olefins process as well as a process for using a quench apparatus. The process removes water from the effluent stream as well as some oxygenate feedstock such as methanol.

U.S. Pat. No. 6,403,854 describes a two stage solids wash and quench for use with the oxygenate conversion process where catalyst fines are removed from the effluent stream through a first quench stage. Water and methanol are removed from the effluent stream in a second quench stage. The quench bottoms from the first quench stage are withdrawn as an aqueous waste stream or drag stream and are sent to a water treatment zone.

It would be desirable if there was a process for operating an oxygenate-to-olefin plant to avoid these problematic consequences. The present invention satisfies these and other needs.

SUMMARY OF THE INVENTION

According to one embodiment, the present invention is a process for removing catalyst fines from a reactor effluent stream from an oxygenate to olefin reactor. The reactor effluent has catalyst fines therein. The process enables the catalyst fines to be removed in an efficient manner. The process comprises withdrawing the reactor effluent stream from the reactor and transporting the reactor effluent stream in a first conduit to a quench device. Then, the reactor effluent stream is quenched with a quench medium in the quench device. The quenching forms a quenched effluent stream and a liquid fraction. The liquid fraction contains a majority of the catalyst fines. The process further comprises transporting the liquid fraction in a second conduit to a solids separation device. In one embodiment, the one-year capacity of the first conduit, second conduit and/or quench device remains within 99 vol % or more based upon an initial capacity of the first conduit, second conduit and/or the quench device.

As used herein, the oxygenate-to-olefins reactor is a reactor that converts oxygenates, such as methanol, to olefins, such as prime olefins. An oxygenate-to-olefins plant is defined as a facility that converts oxygenates to olefins and recovers particular olefin streams with desired olefin content.

In another embodiment, there is a process for recovering one or more olefin product(s) from an oxygenate-to-olefin reactor. The process first comprises withdrawing a reactor effluent stream from the reactor. The reactor effluent stream has catalyst fines therein. The reactor effluent stream is transported in a first conduit to a quench device and is quenched with a quench medium in a quench device to form a quenched effluent stream and a liquid fraction. The liquid fraction comprises a majority of the catalyst fines. The liquid fraction is transported in a second conduit to a solids separation device, wherein the liquid fraction travels through the second conduit at a second velocity ranging from about 1 ft/sec (0.3 m/sec) to about 60 ft/sec (18 m/sec). In the process of one embodiment, one or more olefin product(s) are recovered from the quenched effluent stream.

In yet another embodiment, there is a process for making one or more polymer product(s) from the natural gas. The process comprises the steps of: (a) converting natural gas to an oxygenate; (b) contacting the oxygenate with a molecular sieve catalyst in an oxygenate-to-olefin reactor; (c) withdrawing a reactor effluent stream from the reactor, the reactor effluent stream comprising water and one or more olefin product(s) and having catalyst fines therein; (d) transporting the reactor effluent stream in a first conduit to a quench device, wherein the reactor effluent stream travels through the first conduit at a first velocity of about 100 ft/sec (30 m/sec) or greater; (e) quenching the reactor effluent stream with a quench medium in a quench device to form a quenched effluent stream and a liquid fraction, the liquid fraction comprising the catalyst fines and the water; (f) transporting the liquid fraction in a second conduit to a solids separation device, wherein the liquid fraction travels through the second conduit at a second velocity ranging from about 1 ft/sec (0.3 m/sec) to about 60 ft/sec (18 m/sec); (g) recovering the one or more olefin product(s) from the quenched effluent stream; and (h) polymerizing the one or more olefin product(s) to form the one or more polymer product(s).

There is still another aspect of the present invention comprising a process for making one or more olefin product (s) from a reactor effluent stream that is withdrawn from an oxygenate in an oxygenate-to-olefin reactor, wherein catalyst fines are in a reactor effluent stream and the reactor effluent stream comprises olefin and water. The process comprises the steps of: (a) transporting the reactor effluent stream in a first conduit to a quench device, wherein the reactor effluent stream travels through the first conduit at a first velocity of 100 ft/sec (30 m/sec) or greater; (b) quenching the reactor effluent stream with a quench medium in a quench device to form a quenched effluent stream and a liquid fraction, the liquid fraction comprises the catalyst fines and the water; (c) transporting the liquid fraction in a second conduit to a solids separation device, wherein the liquid fraction travels through the second conduit at a second velocity ranging from about 1 ft/sec (0.3 m/sec) to about 60 ft/sec (1.8 m/sec); and (d) recovering one or more olefin product(s) from the quenched effluent stream.

BRIEF DESCRIPTION OF THE DRAWINGS

FIG. 1 illustrates the overall process of an oxygenate-to-olefins plant according to one embodiment of the present invention.

FIG. 2 illustrates a process for transporting catalyst fines from the oxygenate-to-olefin reactor through the oxygenate-to-olefins plant.

DETAILED DESCRIPTION OF THE INVENTION

Introduction and Overview

The present invention is a process for removing catalyst fines from a reactor effluent stream. The process enables catalyst fines to be removed in an efficient manner. To aid in the understanding of the present invention, a brief overview of the processing steps of producing and using one or more olefin products from an oxygenate feed stream, according to one embodiment, is discussed with reference to FIG. 1. The oxygenate-to-olefin reactor 10 converts an oxygenate feed stream into an olefin product. The gaseous output stream of an oxygenate-to-olefin reactor 10 is defined as the effluent stream. The reactor effluent stream is particularly the gaseous output stream from the point it leaves the reactor 10 to the point it is quenched. The step of quenching 12 cools the effluent stream and removes water and catalyst fines from the effluent stream to produce a quenched effluent stream. Optional compression of the effluent stream is included in the step of quenching 12. A quenched effluent stream is an effluent stream after at least one stage of quenching.

The quenched effluent stream then undergoes a step of washing and drying 14 to produce a dried effluent stream. Washing the quenched effluent stream removes acid components in the effluent stream, such as $CO_2$. Drying removes water that is saturated in the quenched effluent stream. Optionally, the washing and drying stage 14 includes processing steps to remove additional oxygenates.

The dried effluent stream then undergoes a step of recovering the olefin products 16. Particularly, light olefins, i.e. ethylene and propylene, are recovered in an acceptable grade of purity for a particular application. Thereafter, the recovered olefin products are used in various product applications 18. For example, the olefins are used in a polymerization process to make polyolefin products. The present invention is an improvement to the process of making olefins from an oxygenate feed stream. Accordingly, the present invention including a more detailed discussion of each step in the manufacture and use of olefins from an oxygenate feed stream is discussed below.

The Oxygenate-to-Olefin Reaction

As shown in FIG. 2, an-oxygenate feed stream is fed along line 20 into an oxygenate-to-olefin reactor 22 producing a reactor effluent stream that is withdrawn along line 24. The reactor 22 uses a catalyst, for example, a molecular sieve catalyst, made from a molecular sieve catalyst composition. Molecular sieve catalysts are useful for conversion of a feed stream that contains one or more aliphatic-containing compounds. The one or more aliphatic-containing compounds include alcohols, amines, carbonyl compounds, for example, aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feed stream is an oxygenate feed stream. Particularly an oxygenate feed stream is a feed stream that comprises one or more organic compound(s) containing at least one oxygen atom. In the most preferred embodiment of the invention, the oxygenate in the oxygenate feed stream is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols that are useful in the oxygenate feed stream include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the oxygenate feed stream comprises oxygenates selected from one or more of methanol, ethanol, dimethyl ether, diethyl ether or a combination thereof, more preferably methanol and dimethyl ether, and most preferably methanol.

In one embodiment, the oxygenate feed stream is produced from an integrated process for producing oxygenates, particularly alcohols, from a hydrocarbon feedstock, preferably a hydrocarbon gas feedstock, more preferably methane and/or ethane. The first step in the process is passing the gaseous hydrocarbon feedstock, preferably in combination with a water stream, to a synthesis gas production zone to produce a synthesis gas stream. Synthesis gas production is well known, and typical synthesis gas temperatures are in the range of from about 700° C. to about 1200° C. and synthesis gas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol. This purified oxygenate containing stream is used in one embodiment as the oxygenate feed stream. Non-limiting examples of a process for producing an oxygenate feed stream from hydrocarbons and using it to produce olefins is described in EP-B-0 933 345, which is herein fully incorporated by reference.

The various feed streams, preferably oxygenate feed streams, discussed above are converted primarily into one or more olefin(s). The olefin(s) or olefin monomer(s) produced from the feed stream typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof Other olefin monomer(s) include unsaturated monomers, diolefins having 4 to 18 carbon atoms, conjugated or non-conjugated dienes, polyenes, vinyl monomers and cyclic olefins.

In the most preferred embodiment, the feed stream, preferably an oxygenate feed stream, is converted in the presence of a molecular sieve catalyst composition into olefin(s) having 2 to 6 carbons atoms, preferably 2 to 4 carbon atoms. Most preferably, the olefin(s), alone or combination, are converted from an oxygenate feed stream preferably containing an alcohol, and most preferably methanol, to the preferred olefin(s) ethylene and/or propylene often referred to as light olefin(s).

The most preferred oxygenate-to-olefins process is the methanol-to-olefins process. In a methanol-to-olefin process, a methanol containing feed stream is converted to olefins in the presence of a methanol-to-olefins catalyst or catalyst composition. In one embodiment, the methanol-to-olefins catalyst or catalyst composition is molecular sieve catalyst composition.

In one embodiment of the process for conversion of an oxygenate feed stream, the amount of olefin(s) produced based on the total weight of hydrocarbon produced is greater than 50 weight percent, preferably greater than 60 weight percent, more preferably greater than 70 weight percent, and most preferably greater than 75 weight percent.

As noted, oxygenate-to-olefin processes typically use molecular sieve catalysts or molecular sieve catalyst compositions. The molecular sieve catalyst compositions have molecular sieve and binder and/or matrix material. The molecular sieve catalysts are prepared according to techniques that are known to a person of ordinary skill in the art.

Molecular sieves include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, AFO, AEL, EUO, HEU, FER, MEL, MFI, MTW, MTT, TON, EMT, FAU, ANA, BEA, CFI, CLO, DON, GIS, LTL, MER, MOR, MWW and SOD and substituted forms thereof, and the large pore molecular sieves. Preferably, the molecular sieve is a zeolitic or zeolitic-type molecular sieve. Alternatively, the preferred molecular sieve is an aluminophosphate (ALPO) molecular sieves and/or silicoaluminophosphate (SAPO) molecular sieves and substituted, preferably metal substituted, ALPO and/or SAPO molecular sieves including the molecular sieves that are intergrowth materials having two or more distinct phases of crystalline structures within one molecular sieve composition.

Binder materials that are useful alone or in combination include various types of hydrated alumina, silicas, and/or other inorganic oxide sol. In one embodiment, the binders are alumina sols including Nalco 8676 available from Nalco Chemical Co., Naperville, Ill., and Nyacol available from The PQ Corporation, Valley Forge, Pa.

Matrix materials include one or more of: rare earth metals, metal oxides including titania, zirconia, magnesia, thoria, beryllia, quartz, silica or sols, and mixtures thereof, for example, silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feed stream, preferably an oxygenate feed stream, in one embodiment, contains one or more diluents, typically used to reduce the concentration of the active ingredients in the feed stream, and are generally non-reactive to the active ingredients in the feed stream or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feed stream entering into a reactor or added directly into the reactor, or added with a molecular sieve catalyst composition. In one embodiment, the amount of diluent in the feed stream is in the range of from about 1 to about 99 mole percent, preferably from about 1 to 80 mole percent, more preferably from about 5 to about 50, and most preferably from about 5 to about 25 diluent based on the total number of moles of the active components of the feed stream plus diluent in the feed stream.

In one embodiment, other hydrocarbons are added to the feed stream, preferably oxygenate feed stream, either directly or indirectly, and include olefin(s), paraffin(s), aromatic(s) (see for example, U.S. Pat. No. 4,677,242, addition of aromatics) or mixtures thereof, preferably propylene, butene, pentene, and other hydrocarbons having 4 or more carbon atoms, or mixtures thereof.

The process for converting a feed stream, especially an oxygenate feed stream in the presence of a molecular sieve catalyst composition is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in, for example, U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred oxygenate-to-olefin reactor is a riser reactor. Riser reactors are generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor, a regenerator, and a recovery system.

The reactor or reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Feed stream, preferably an oxygenate feed stream, optionally with one or more diluent(s), is fed to the one or more riser reactor(s) in which a zeolite, zeolite-type molecular sieve catalyst, silicaluminophosphate catalyst composition or coked version thereof is introduced. In one embodiment, the molecular sieve catalyst composition or coked version thereof is contacted with a liquid or gas, or combination thereof, prior to being introduced to the riser reactor(s). Preferably, the liquid is water or methanol, and the gas is an inert gas such as nitrogen.

In an embodiment, the feed stream, preferably an oxygenate feed stream, is fed into the reactor in the vapor form or the liquid form. The vapor form of the feed stream is referred to as a vapor feed stream. The feed stream in the liquid form is referred to as the liquid feed stream. The amount of liquid feed stream fed separately or jointly with a vapor feed stream, to a reactor system is in the range of from 0.1 weight percent to about 85 weight percent, preferably from about 1 weight percent to about 75 weight percent, more preferably from about 1 weight percent to about 10 weight percent based on the total weight of the feed stream including any diluent contained therein. The liquid and vapor feed streams are preferably of similar composition, or contain varying proportions of the same or different feed stream compositions with varying proportions of the same or different diluent compositions.

The feed stream, preferably an oxygenate feed stream, entering the reactor system is preferably converted, partially or fully, in the first reactor zone into an effluent stream that enters the disengaging vessel along with a coked molecular sieve catalyst composition. In the preferred embodiment, particle size separators within the disengaging vessel are designed to separate catalyst particles from the effluent stream containing one or more olefin(s) within the disengaging zone as well as separate catalyst particles from catalyst fines in the effluent stream. Cyclones are preferred particle size separators. Cyclones retain catalyst particles but do not retain catalyst fines.

Gravity effects within the disengaging vessel will also separate the catalyst particles from the effluent stream. Other methods for separating the catalyst particles from the effluent stream include the use of plates, caps, elbows, and the like.

In one embodiment, the reactor effluent stream as it leaves the reactor comprises ethylene and propylene, $C_4$+olefins, methane, $C_2$+parrafins, water, unreacted oxygenate feed stream, and oxygenate hydrocarbons. In another embodiment, the reactor effluent stream comprises from about 30 wt. % to about 70 wt. % water, preferably, from about 35 wt. % to about 70 wt. % water; more preferably from about 40 wt. % to about 65 wt. % water expressed as a percentage of the total weight of the reactor effluent stream. According to another aspect of the invention, there are catalyst fines in the reactor effluent stream. The weight of catalyst fines in the reactor effluent stream, including catalyst fines, expressed as a percent of the weight of the reactor effluent stream plus catalyst fines comprises about 5 wt. % or less, preferably about 2 wt. % or less, more preferably about 1 wt. % or less; even more preferably about 0.5 wt. % or less. In another embodiment, the weight of the catalyst, including catalyst fines, expressed as a percentage of the weight of the reactor effluent stream plus catalyst fines comprises from about 0.00005 wt. % to about 0.5 wt. %; preferably; from about 0.0001 wt. % to about 0.1 wt. %.

In one embodiment, the catalyst fines have a particle density ranging from about 60 lbs/ft$^3$ (960 kg/m$^3$) to about 150 lbs/ft$^3$ (2400 kg/m$^3$), preferably from about 70 lbs/ft$^3$ (1100 kg/m$^3$) to about 125 lbs/ft$^3$ (2000 kg/m$^3$), more preferably from about 75 lbs/ft$^3$ (1200 kg/m$^3$) to about 100 lbs/ft$^3$ (kg/m$^3$). In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 hr$^{-1}$ to about 20,000 hr$^{-1}$ based on the volume of gas to volume of coked molecular sieve catalyst composition, preferably at an elevated temperature from about 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C., and most preferably from about 350° C. to about 550° C.

The conversion pressure employed in the conversion process, specifically within the reactor system, varies over a wide range including autogenous pressure. The conversion pressure is based on the partial pressure of oxygenate in the oxygenate feed stream exclusive of any diluent therein. Typically, the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting an oxygenate feed stream in the presence of a molecular sieve catalyst composition within a reaction zone, is defined as the total weight of the oxygenate feed stream excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of an oxygenate feed stream containing methanol and dimethyl ether is in the range of from about 20 hr$^{-1}$ to about 300 hr$^{-1}$.

The superficial gas velocity (SGV) of an oxygenate feed stream including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example, U.S. patent application Ser. No. 09/708,753 filed Nov. 8, 2000, which is herein incorporated by reference.

In one preferred embodiment of the process for converting an oxygenate-to-olefin(s) using a silicoaluminophosphate molecular sieve catalyst composition, the process is operated at a WHSV of at least 20 hr$^{-1}$ and a Temperature Corrected Normalized Methane Selectivity (TCNMS) of less than 0.016, preferably less than or equal to 0.01. See, for example, U.S. Pat. No. 5,952,538 that is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The process of converting oxygenates to olefins with certain molecular sieve catalyst compositions causes carbonaceous deposits or "coke" to build up on the catalyst. With continued reference to FIG. 2 describing one embodiment of the present invention, the coked molecular sieve catalyst or coked catalyst is withdrawn from a disengaging vessel of the reactor 22, preferably by one or more cyclones (s). The coked catalyst travels along line 23 and is introduced into a regenerator 21. In the regenerator 21, the coked catalyst is contacted with a regeneration medium, preferably a gas containing oxygen, under general regeneration conditions of temperature, pressure, and residence time.

Non-limiting examples of a regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kpaa) to about 150 psia (1034 kPaa), and most preferably from about 30 psia (207 kPaa) to about 60 psia (414 kPaa).

The preferred residence time of a catalyst, including a molecular sieve catalyst, in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example, with coked catalyst. Also, in another embodiment, fresh molecular sieve catalyst is added to the regenerator containing a regeneration medium of oxygen and water as described in U.S. Pat. No. 6,245,703, which is herein fully incorporated by reference.

With continued reference to FIG. 2 illustrating one embodiment, the burning of catalyst including catalyst particles in the regenerator 21 produces a flue gas and regenerated catalyst, including regenerated catalyst particles and regenerated catalyst fines. The flue gas is defined as the gaseous output of the regenerator 21. The flue gas is separated from the regenerated catalyst particles by a particle size separator such as a cyclone. Cyclones retain catalyst particles but allow the flue gas to exit the regenerator 21 along line 50. Additionally, regenerated catalyst fines are carried in the flue gas and leave the regenerator 21.

Once the flue gas and regenerated catalyst fines exit the regenerator 21 along line 50, they are optionally cooled in a heat exchanger (not shown). The regenerated catalyst fines are separated in a scrubber 52. A scrubber medium, such as an aqueous composition such as boiler feed water, quench water, or fresh water, is fed into the scrubber 52 along line 53. The scrubber medium contacts the regenerated catalyst fines in the flue gas and washes the regenerated catalyst fines from the flue gas into a scrubber bottoms stream, which is conveyed along line 56. The scrubber bottoms stream can be treated in a settling device according to the principles of the present invention described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst from the regeneration system and passing the regenerated catalyst through a catalyst cooler that forms a cooled regenerated catalyst. The catalyst cooler, in an embodiment, is a heat exchanger that is located either internal or external to the regeneration system.

In one embodiment, the cooler regenerated catalyst is returned to the regenerator in a continuous cycle, alternatively, (see U.S. patent application Ser. No. 09/587,766 filed Jun. 6, 2000) a portion of the cooled regenerated catalyst is returned to the regenerator vessel in a continuous cycle, and another portion of the cooled regenerated catalyst is returned to the riser reactor(s), directly or indirectly, or a portion of the regenerated catalyst or cooled regenerated catalyst is contacted with by-products within the effluent stream (PCT WO 00/49106 published Aug. 24, 2000), which are all herein fully incorporated by reference. In another embodiment, a regenerated catalyst contacted with an alcohol, preferably ethanol, 1-propanol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

Referring again to FIG. 2, the regenerated catalyst particles are withdrawn from the regenerator 21 and returned to the reactor 22 along line 25. In another embodiment, the regenerated catalyst particles withdrawn from the regeneration system are returned to the riser reactor(s) directly or optionally after passing through a catalyst cooler. In one embodiment, a carrier, such as an inert gas, vapor feed stream, steam or the like, semi-continuously or continuously, facilitates the introduction of the regenerated catalyst to the reactor or reactor system, preferably to the one or more riser reactor(s).

In one embodiment, the optimum level of coke on the catalyst composition in the reaction zone is maintained by controlling the flow of the regenerated catalyst or cooled regenerated catalyst from the regeneration system to the reactor system. There are many techniques for controlling the flow of a catalyst described in Michael Louge, *Experimental Techniques, Circulating Fluidized Beds*, Grace, Avidan and Knowlton, eds., Blackie, 1997 (336–337), which is herein incorporated by reference. This is referred to as the complete regeneration mode. In another embodiment, the optimum level of coke on the molecular sieve catalyst in the reaction zone is maintained by controlling the flow rate of the oxygen-containing gas flow to the regenerator. This is referred to as the partial regeneration mode.

Coke levels, or the level of carbonaceous deposits on the catalyst, are measured by withdrawing from the conversion process the catalyst composition at a point in the process and determining its carbon content.

In one preferred embodiment, the catalyst in the reaction zone contains in the range of from about 1 to about 50 weight percent, preferably from about 2 to about 30 weight percent, more preferably from about 2 to about 20 weight percent, and most preferably from about 2 to about 10 weight percent coke or carbonaceous deposit based on the total weight of the mixture of catalyst. See for example, U.S. Pat. No. 6,023,005, which is herein fully incorporated by reference. It is recognized that the catalyst in the reaction zone is made up of a mixture of regenerated catalyst and catalyst that has ranging levels of carbonaceous deposits. The measured level of carbonaceous deposits thus represents an average of the levels an individual catalyst particle.

In the embodiment illustrated in FIG. 2, the reactor effluent stream leaves the reactor 22 through particle size separators and travel along line 24. The reactor effluent stream contains catalyst fines. According to one embodiment, the reactor effluent stream has about 2 wt. % or less, preferably about 1 wt. % or less, more preferably from about 0.05 wt. % to about 1 wt. % catalyst fines based upon the total weight of the reactor effluent stream.

According to one embodiment, about 90 wt. % or more, preferably 95 wt. % or more, most preferably 98 wt. % or more of the catalyst fines have a particle size less than 40 microns, based upon the total weight of the catalyst fines as they leave the reactor. According to another embodiment, about 75 wt. % or more of the catalyst fines, preferably about 80 wt. % or more of the catalyst fines, more preferably about 85 wt. % or more of the catalyst fines have a particle size of about 20 microns or less, based upon the total weight of the catalyst fines.

The reactor effluent stream is transported in a first conduit to a quench device. The first conduit is defined as the conduit that conveys the reactor effluent stream from the reactor to the quench device. The first conduit has a capacity including an initial capacity and a one-year capacity. The initial capacity is defined as the capacity of flow through conduit or equipment under particular operating conditions at the time the system starts operation and flow of medium begins through the conduit or equipment. Such a start up could be the initial plant start up or a restart after service and maintenance of the equipment including cleaning the conduit or equipment.

The one-year capacity is the capacity of the conduit or equipment after operation of at least one-year of continuous operation. The one-year capacity is tested under the particular operating conditions that existed at the time the system started up. According to one embodiment, the one-year capacity of the first conduit, second conduit and/or quench device remain within 95 vol. % or more, preferably within 98 vol. %, more preferably within 99 vol. %, and most preferably within 99.5 vol. % based upon the starting capacity.

According to one embodiment, the first conduit is configured with bends in the conduit as needed to convey the reactor effluent stream from the reactor through optional heat exchangers to the quench device. In one embodiment, illustrated in FIG. 2, a bend is shown in line 24 by way of example and not by imitation. According to one embodiment, the first conduit has a conduit diameter and has one or more bends each having a bend radius. The ratio of the bend radius to the conduit diameter is about 1:1 or greater, preferably from about 1:1 to about 4:1, more preferably from about 1:1 to about 2:1. The conduit diameter is the diameter of the conduit assuming that the cross section of the conduit is generally a circle. In the case where a conduit is not circular, it would be understood by a person of ordinary skill in the art that an effective conduit diameter can be mathematically derived based upon the cross sectional area of the pipe at the point of the bend. The effective conduit diameter can be calculated by dividing the cross sectional area by the constant pi and taking the square root of the resulting quotient. For the purpose of the present invention, conduit diameter includes effective conduit diameter.

The bend radius is the radius of the bend determined at the centerline of the conduit.

According to one embodiment, the reactor effluent stream has a dewpoint. Dewpoint is the temperature that a gaseous stream first condenses. The reactor effluent stream remains at a temperature above the dewpoint while it is transported from the reactor effluent stream to the quench device in the first conduit.

According to the present invention, the reactor effluent stream travels through line 24 at a velocity of about 100 ft/sec (30 m/sec) or greater, preferably from about 100 ft/sec (30 m/sec) to about 300 ft/sec (90 m/sec); and more preferably from about 100 ft/sec (30 m/sec) to about 200 ft/sec (60 m/sec). The control of the velocity that the reactor effluent stream travels through line 24 according to the present invention reduces accumulation of catalyst fines within line 24 and/or reduces the erosion of line 24.

In one embodiment illustrated in FIG. 2, the first conduit is in fluid communication with a heat exchanger system 26. According to one embodiment, the heat exchanger system 26 comprises one or more heat exchanger services, preferably two to four heat exchanger services, most preferably two or three heat exchanger services. Optionally, the heat exchanger system 26 cools the effluent stream to produce a cooled effluent stream. Cooled effluent stream is an effluent stream after at least one stage of cooling before at least one stage of quenching. The reactor effluent stream travels through the one or more heat exchanger at a velocity of about 100 ft/sec (30 m/sec) or greater, preferably from about 100 ft/sec (30 m/sec) to about 300 ft/sec (90 m/sec); and more preferably from about 100 ft/sec (30 m/sec) to about 200 ft/sec (60 m/sec).

The cooled effluent stream is withdrawn from the heat exchanger system 26 along line 28. The cooled reactor effluent stream is sent to a quench device 30.

Quench, Compression, and Catalyst Fines Separation from Quench Bottoms

The reactor effluent stream, of one embodiment, travels along line 28 where it is quenched with a quench medium in a quench device. The result is a quench effluent stream, which is defined as an effluent stream after at least one stage of quenching and before the stage of washing. According to FIG. 2, the quench device is represented by a two stage quench system. The first quench device 30 is a pre-quench stage. The second quench device 57 is an additional quench stage.

Generally, the quenching forms a quenched effluent stream and a liquid fraction. The quenched effluent stream is gaseous and, in one embodiment, leaves the first quench device 30 along line 32. The liquid fraction contains a majority of the catalyst fines that were in the reactor effluent stream. The process further comprises transporting the liquid fraction in a second conduit (as represented in FIG. 2 by line 34) to a solids separation device 36.

The step of quenching is needed to remove a substantial amount of water from the reactor effluent stream and remove a substantial amount of catalyst fines that are in the effluent stream. Among other things, water and catalyst fines are removed from the reactor effluent stream by a quench device 30. A "quench device" is a device for removing a portion of the reactor effluent stream by establishing a sufficient quantity of liquid quench medium in contact with a gaseous reactor effluent stream which condenses at least a portion of the material in the reactor effluent stream. One example of a quench device in an oxygenate-to-olefin product stream is found in U.S. Pat. No. 6,121,504 (direct product quench) fully incorporated herein by reference. A "quench medium" is defined as a liquid that contacts the effluent stream in a quench device.

In a quench device, at least a portion of the effluent stream is rapidly condensed through contact with the quench medium. When quenching in a quench device, at least a portion of the reactor effluent stream remains in a gaseous state. A portion of the reactor effluent stream condenses to forms a liquid fraction. In one embodiment, the liquid fraction is withdrawn from the first quench device as a first liquid fraction along line 34.

In one embodiment, a majority of the catalyst fines in the reactor effluent stream is removed in the first liquid fraction of the first quench device 30. The term "majority" means more than 50%. The bottoms stream of the first phase quench or pre-quench comprises a relatively concentrated amount of catalyst fines compared to a quench device that is operated to remove all of the water in the effluent stream in one stage. According to one embodiment, the weight of the catalyst fines in the first liquid fraction is about 5 wt. % or less, preferably about 2 wt. % or less, more preferably about 0.1 wt. % or less based on the total weight of the first liquid fraction. According to one embodiment, the weight of catalyst fines in the first liquid fraction is about 10 wppm or greater based upon the total weight of the first liquid fraction.

Additionally, the compounds in the reactor effluent stream, that are liquid under quenching conditions typically comprises water, a portion of the unreacted oxygenate feed stream (typically methanol), and a small portion of the oxygenate conversion byproducts, e.g. heavy hydrocarbons (C5+) form the liquid fraction.

The portion of the reactor effluent stream in a gaseous state is separated from the first liquid fraction and forms the quenched effluent stream. According to FIG. 2, the quenched effluent stream is withdrawn from the first quench device 30 along line 32 in one embodiment.

The portion of the reactor effluent stream that is gaseous under quenching conditions typically comprises light olefins, dimethyl ether, methane, CO, $CO_2$, ethane, propane, and any water and unreacted oxygenate feed stream that is not condensed during the operation of the quench device.

In one embodiment, a quench medium is introduced to the first quench device 30 along line 33. According to one embodiment, the quench medium has low levels of catalyst fines in the quench medium. Particularly, the quench medium has the same amount of catalyst fines as the quench bottoms, according to one embodiment. Low levels of catalyst fines in the quench medium prevent accumulation of catalyst fines in the quench device or quench tower.

The quench medium, according to one method of use, is introduced into the quench device at a location or locations above where the reactor effluent stream is introduced, such that the quench medium will fall within the quench device and be contacted with the reactor effluent stream as it, or portions of it including the olefins in a gaseous state, rise through the device.

The quench device typically includes internal elements in a contact zone to facilitate intimate contacting of the quench medium with the reactor effluent stream or portions thereof. Contact zone is defined as the zone of the quench device where the effluent stream comes in contact with the quench medium.

Internal elements include liquid distributors and contacting devices such as baffles, trays or structured packing. In one embodiment, the use of structured packing in the quench device can ensure that catalyst fines do not accumulate in the quench device. Structured packing is a construction of material bound into fixed shapes built for the purpose of facilitating vapor liquid contacting. Examples of structured packing include but are not limited to gauze packing, bent metals, corrugated metals or punched metals, ceramic packing and plastic packing.

In a particular embodiment, the quench medium is water. In another embodiment, the quench medium is a portion of the water that has been recovered from the bottoms stream of a quench device, cooled and reintroduced to the quench tower. In one embodiment, the quench medium is supplied along line 33 to the first quench device 30.

One aspect of a two stage quench embodiment is shown in FIG. 2. The first quench device 30 produces a quenched effluent stream withdrawn along line 32 (also known as a first quenched effluent stream). The overhead stream is directed to the second quench device. The second quench device separates the first quenched effluent stream into a second quenched effluent stream and a second liquid fraction. The second quench device of one embodiment functions to de-water the first quenched effluent stream. The second quench device condenses substantially all of the remaining water vapor in the first quenched effluent stream and produces a second quenched effluent stream withdrawn along line 64. Since, most of the solids have been previously removed in the first quench device, the first quenched effluent stream is relatively free of solids compared to the reactor effluent stream. Accordingly, the second liquid fraction is relatively free of catalyst fines compared to the first liquid fraction. Thus, the composition of the second liquid fraction makes a quench medium that prevents accumulation of catalyst fines within the quench device. According one embodiment of FIG. 2, at least a portion of the second liquid fraction is withdrawn along line 58. The second liquid fraction is cooled in a heat exchanger 60 and recycled to the second quench device 56. An additional portion of the cooled second liquid fraction is withdrawn along line 62 where it supplies line 33 as a quench medium for the first quench device.

The second quenched effluent stream is an olefin stream that has little more water than the saturation level of the quenched effluent stream. According to one embodiment, the amount of catalyst fines in the second quenched effluent stream is no greater than about 80 wppm; preferably no greater than 20 wppm; more preferably no greater than about 10 wppm based upon the total weight of the second quenched effluent stream. Following the second phase quench, the second quenched effluent stream, typically, is directed to a compression train, caustic wash, dryers and the recovery train as described below.

With continued reference to FIG. 2, the first liquid fraction is withdrawn from the first quench device 30 along line 34 to a settling tank 36. Furthermore, at least a portion of the second liquid fraction is withdrawn from the second quench device 56 along line 68. The second liquid fraction is transported along line 68 to a settling tank 36. In one embodiment, lines 34 and 68 are combined into a single stream before transporting to the settling tank 36. According to one embodiment, a step of transporting catalyst fines in a liquid medium through a second conduit comprising the first liquid fraction and/or the second liquid fraction occurs at a second velocity of from about 1 ft/sec (0.3 m/sec) to about 60 ft/sec (18 m/sec), preferably from about 1 ft/sec (0.3 m/sec) to about 40 ft/sec (12 m/sec), and more preferably from about 2 ft/sec 0.6 m/sec) to about 10 ft/sec (9 m/sec).

A settling tank is a solids separation device. According to one embodiment, the settling tank is replaced by another solids separation device. A solids separation device is any device that separates solids from liquid by the difference in the density of the solid and liquid. Examples of separation devices include settling devices and centrifugal separators such as a centrifuge. A settling device is defined as a device that separates solid particulate from liquid using gravitational force. According to one embodiment, the settling device is selected from the group consisting of clairifiers, settling tanks, and settling ponds.

With continued reference to FIG. 2, the first liquid fraction and the second liquid fraction are transported to a settling tank 36. In another embodiment, regenerated catalyst fines and scrubber medium from the scrubber 52 is conveyed along line 57 to settling tank 36. Alternatively, the regenerated catalyst fines and scrubber medium is combined with line 34 and/or line 68.

The catalyst fines are separated from the first liquid fraction by settling the catalyst fines to the bottom of the settling tank 36 forming concentrated catalyst fines and a first liquid portion. The first liquid portion is the liquid remaining after sedimentation of the catalyst fines in the settling tank 36. The concentrated catalyst fines are withdrawn along line 40.

To aid in the efficient removal of catalyst fines from the first liquid fraction, a flocculent is added, in one embodiment, through line 38. Flocculent is defined as material added to a liquid and solids mixture, which enhances the density differences between the solid and liquid and hence improves the sedimentation process. The flocculent enhances the settling of the catalyst fines to the bottom of the settling tank 36. According to one embodiment, the time it takes for effective separation with the flocculent is about 2.5 hours or less, preferably about 2.0 hours or less, more preferably about 1.5 hours or less, most preferably about 1.0 hours or less. Effective separation as used herein pertains to separation of a liquid portion from a solid portion in a liquid/solid mixture. Effective separation occurs when a liquid portion is isolated from the solid liquid mixture, so that the liquid portion contains about 1 wt. % or less of the solids that were present in the solid/liquid mixture.

According to one embodiment, the first liquid portion has a concentration of catalyst fines that is less than the concentration of catalyst fines in the first liquid fraction because of the settling. In one embodiment, the flocculent is a cationic polymer. Preferably, the flocculent is a cationic polymer selected from the group consisting of: polyacryamides, diallyldimethyl amonium chloride, epichlorohydrin-amine, and dicandiamide-formaldehyde.

According to one embodiment, the ratio of the weight of the catalyst fines to the weight of the flocculent is less than the amount at which the given flocculent results in overdosing. Overdosing occurs when more flocculent is added than is needed to settle the solid particles. Overdosing is often measured by the presence of flocculent in the activated sludge or water stream.

The first liquid portion is withdrawn from the settling device along line 42. According to one embodiment, the level of catalyst fines in the first liquid portion is significantly less than the level of catalyst fines in the combined stream selected from the group comprising the first liquid fraction, second liquid fraction and scrubber medium or one of the individual streams. In another embodiment, the level of catalyst fines in the first liquid portion is substantially less than the level of catalyst fines in the combined stream. According to another embodiment, the first liquid portion is substantially free of catalyst fines. According to another embodiment, the first liquid portion is clarified.

In one embodiment, the first liquid portion is conveyed to a settling pond 44 along line 42. The catalyst fines are separated from the first liquid portion by settling the catalyst fines to the bottom of the settling pond 44 forming concentrated catalyst fines and a second liquid portion. The second liquid portion is the liquid fraction resulting from the sedimentation of the catalyst fines in the settling pond 44.

To aid in the efficient removal of catalyst fines from the combined fraction, a flocculent, optionally, is added along line 46. The flocculent enhances the settling of the catalyst fines to the bottom of the settling pond. According to one embodiment, the time it takes for effective separation with the flocculent is about 2.5 hours or less, preferably about 2.0 hours or less, more preferably about 1.5 hours or less, most preferably about 1.0 hours or less. In one embodiment the flocculent is a cationic polymer. Preferably, the flocculent is a cationic polymer selected from the group consisting of: polyacryamides, diallyldimethyl amonium chloride, epichlorohydrin-amine, and dicandiamide-formaldehyde.

The second liquid portion has a concentration of catalyst fines that is less than the concentration of catalyst fines in the first liquid portion because of the settling. The second liquid portion is withdrawn from the settling device along line 48. According to one embodiment, the third liquid fraction is clarified. The third liquid fraction flows along line 48 where the water is further processed for reuse or safe release into the environment.

As previously described the reactor effluent stream is quenched to remove catalyst fines and water in the reactor effluent stream and produces a quenched effluent stream. The quenched effluent stream is further processed by washing to remove acid gases and alternatively other oxygenates and drying to remove water as described below.

Product Wash and Drying

An acid gas wash is used to remove acid gas from the quenched effluent stream in the first fraction by contacting the first fraction with an acid gas absorbent or adsorbent according to one embodiment. Examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions, which are useful in an embodiment of this invention, contain any amine compound or compounds suitable for acid gas absorption. Examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations can range from about 0.5 to about 8 moles of amine per liter of aqueous solution.

Piperazine and/or monomethylethanolamine (MMEA) can be added to aqueous amine solutions to enhance their absorption capabilities. These additives are included in the aqueous solution at a concentration of from about 0.04 to about 2 moles per liter of aqueous solution in one embodiment of the invention.

Caustic compounds, which can be used in this invention, are alkaline compounds, which are effective in removing acid gas from an olefin stream. Non-limiting examples of such alkaline compounds include sodium hydroxide and potassium hydroxide.

Following acid gas treating, it is desirable to remove additional material in the quenched effluent stream using a water wash. Conventional equipment can be used. It is desirable, however, to further remove additional water from the quenched effluent streams.

A drying step is optionally included. In this embodiment, a solid or liquid drying system can be used to remove water and/or additional oxygenated hydrocarbon from the quenched effluent stream.

In the solid drying system, the quenched effluent stream having been optionally acid gas treated and water washed, is contacted with a solid adsorbent to further remove water and oxygenated hydrocarbon to very low levels. Typically, the adsorption process is carried out in one or more fixed beds containing a suitable solid adsorbent.

Adsorption is useful for removing water and oxygenated hydrocarbons to very low concentrations, and for removing oxygenated hydrocarbons that may not normally be removed by using other treatment systems. Preferably, an adsorbent system used as part of this invention has multiple adsorbent beds. Multiple beds allow for continuous separation without the need for shutting down the process to regenerate the solid adsorbent. By way of example and not by limitation, a three bed system typically has one bed that is on-line, one bed regenerated off-line, and a third bed on stand-by.

The specific adsorbent solid or solids used in the adsorbent beds depends on the types of contaminants being removed. Non-limiting examples of solid adsorbents for removing water and various polar organic compounds, such as oxygenated hydrocarbons and absorbent liquids, include aluminas, silica, 3A molecular sieves, 4A molecular sieves, and alumino-silicates. Beds containing mixtures of these sieves or multiple beds having different adsorbent solids are used to remove water, as well as a variety of oxygenated hydrocarbons in one embodiment.

In an embodiment of this invention, one or more adsorption beds are arranged in series or parallel. In one example of a series arrangement, a first bed is used to remove the smallest and most polar molecules, which are the easiest to remove. Subsequent beds for removing larger less polar oxygenated species are next in series. As a specific example of one type of arrangement, water is first selectively removed using a 3A molecular sieve. This bed is then followed by one or more beds containing one or more less selective adsorbents such as a larger pore molecular sieve e.g. 13X and/or a high surface area active alumina such as Selexorb CD (Alcoa tradename).

In another embodiment, the first bed is a 3.6A molecular sieve capable of selectively removing both water and methanol. This bed can then be followed by one or more 13X or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the quenched effluent stream. The water absorbent can be any liquid effective in removing water from an olefin stream. Preferably, the water absorbent is a polyol or an alcohol, such as ethanol or methanol.

Preferably the olefin from the adsorption beds contains less than about 100 wppm water, more preferably less than about 10 wppm, and most preferably less than 1 wppm. Preferably less than about 10 wppm dimethyl ether is present in the stream leaving the adsorption beds, more preferably less than about 5 wppm, and most preferably less than about 1 wppm. The step of acid washing and drying produces a dried olefin stream.

Product Recovery

The dried olefin stream, or olefin product stream, is further processed to isolate and purify components in the effluent stream, particularly, ethylene and propylene. There are many well-known recovery systems, techniques and sequences that are useful in separating olefin(s) and purifying olefin(s) in the dried effluent stream. Recovery systems generally comprise one or more or a combination of a various separation, fractionation and/or distillation towers, columns, splitters, or trains, reaction systems and other associated equipment, for example, various condensers, heat exchangers, refrigeration systems or chill trains, compressors, knock-out drums or pots, pumps, and the like.

Non-limiting examples of equipment used in a recovery system include one or more of a demethanizer, preferably a high temperature demethanizer, a dethanizer, a depropanizer, a wash tower often referred to as a caustic wash tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in an oxygenate-to-olefin process are passed through a purification system that removes low levels of by-products or contaminants.

Non-limiting examples of contaminants and by-products include generally polar compounds such as water, alcohols, carboxylic acids, ethers, carbon oxides, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example, for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in, for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent stream withdrawn from the reactor or converting those products produced as a result of the recovery system utilized.

In one embodiment, the olefin product stream is passed through a recovery system producing one or more hydrocarbon containing stream(s), in particular, a three or more carbon atom ($C_3^+$) hydrocarbon containing stream. In this embodiment, the $C_3^+$ hydrocarbon containing stream is passed through a first fractionation zone producing a crude $C_3$ hydrocarbon and a $C_4^+$ hydrocarbon containing stream, the $C_4^+$ hydrocarbon containing stream is passed through a second fractionation zone producing a crude $C_4$ hydrocarbon and a $C_5^+$ hydrocarbon containing stream. The four or more carbon hydrocarbons include butenes such as butene-1 and butene-2, butadienes, saturated butanes, and isobutanes.

The effluent stream removed from a conversion process, particularly an oxygenate-to-olefin process, typically has a minor amount of hydrocarbons having 4 or more carbon atoms. The amount of hydrocarbons having 4 or more carbon atoms is typically in an amount less than 30 weight percent, preferably less than 25 weight percent, more preferably less than 20 weight percent, and most preferably less than 15 weight percent, based on the total weight of the effluent stream withdrawn from an oxygenate-to-olefin process, excluding water. In particular with a conversion process of oxygenates into olefin(s) utilizing a molecular sieve catalyst composition the resulting effluent stream typically comprises a majority of ethylene and/or propylene and a minor amount of four carbon and higher carbon number products and other by-products, excluding water.

The preferred light olefin(s) produced by any one of the processes described above, preferably conversion processes, are high purity prime olefin(s) products that contains a $C_x$ olefin, wherein x is a number from 2 to 4, in an amount greater than 80 wt. %, preferably greater than 90 wt. %, more preferably greater than 95 wt. %, and most preferably no less than about 99 wt. %, based on the total weight of the olefin. The purity of the olefins is preferably of a grade that makes the use of the olefins acceptable for one or more applications discussed below.

Olefin Product Use

Suitable well-known reaction systems that follow the recovery system primarily take lower value products and convert them to higher value products. For example, the $C_4$ hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel.

Non-limiting examples of reaction systems that take lower value products and convert them to higher value products include U.S. Pat. No. 5,955,640 (converting a four carbon product into butene-1), U.S. Pat. No. 4,774,375 (isobutane and butene-2 alkylated to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all herein fully incorporated by reference.

Other uses for one or more olefin products are disclosed in U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent stream fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In another embodiment, olefin(s) produced are directed to, in one embodiment, one or more polymerization processes for producing various polyolefins. (See for example, U.S. patent application Ser. No. 09/615,376 filed Jul. 13, 2000 that is herein fully incorporated by reference.)

Polymerization processes include solution, gas phase, slurry phase and a high-pressure process, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352,749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281,300 describe slurry phase polymerization processes; U.S. Pat. Nos. 4,271,060, 5,001,205, 5,236,998 and 5,589,555 describe solution phase polymerization processes; and U.S. Pat. Nos. 3,917,577, 4,175,169, 4,935,397, and 6,127,497 describe high pressure polymerization processes; all of which are herein fully incorporated by reference.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076,698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the present invention comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kPag) to greater than about 1000 psig (3448 kPag), preferably in the range of from about 200 psig (1379 kPag) to about 500 psig (3448 kPag), and more preferably in the range of from about 250 psig (1724 kPag) to about 350 psig (2414 kPag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene-based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight ($M_w/M_n$) of greater than 1.5 to about 10 as measured by gel permeation chromatography, a melt index ($I_2$) as measured by ASTM-D-1238-E in the range from 0.01 dg/min to 1000 dg/min, a melt index ratio ($I_{21}/I_2$) (I21 is measured by ASTM-D-1238-F) of from 10 to less than 25, alternatively a $I_{21}/I_2$ of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multi-layered constructions in the form of bottles, vessels, large hollow articles, rigid food containers and toys, etc.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

The foregoing description of the invention including but not limited to drawing and example are intended to illustrate one or more embodiments of the invention and are non-limiting. While the invention has been illustrated an described herein in terms of the advantages, features, and applications disclosed, it will be apparent to a person of ordinary skill in the art that the invention can be used in other instances. Other modifications and improvements can be made without departing from the scope of the invention.

What is claimed is:

1. A process for removing catalyst fines from an effluent stream from an oxygenate-to-olefin reactor, the process comprising:
    (a) withdrawing the reactor effluent stream from the reactor;
    (b) transporting the reactor effluent stream in a first conduit to a quench device, wherein the reactor effluent stream travels through the first conduit at a first velocity of about 100 ft/sec (30 m/sec) or greater, and wherein the first conduit has a conduit diameter and has one or more bends each having a bend radius, such that a ratio of the bend radius to the conduit diameter is about 1:1 or greater;
    (c) quenching the reactor effluent stream with a quench medium in the quench device to form a quenched effluent stream and a liquid fraction, the liquid fraction containing a majority of the catalyst fines; and
    (d) transporting the liquid fraction in a second conduit to a solids separation device.

2. The process of claim 1, wherein the quench medium has about 1 wt. % or less catalyst fines based upon the total weight of the quench medium.

3. The process of claim 1, wherein the quench device has a contact zone with structured packing.

4. The process of claim 1, wherein the first conduit has a conduit diameter and has one or more bends each having a bend radius, wherein a ratio of the bend radius to the conduit diameter is about 2.0:1.0 or greater.

5. The process of claim 1, wherein the reactor effluent stream has a dewpoint and the reactor effluent stream remains at a temperature above the dewpoint during the step (b) of transporting.

6. The process of claim 1, wherein the first velocity is from about 100 ft/sec (30 m/sec) to about 300 ft/sec (90 m/sec).

7. The process of claim 1, wherein the first velocity is from about 100 ft/sec (30 m/sec) to about 200 ft/sec (60 m/sec).

8. The process of claim 1, wherein about 95 wt. % or more of the catalyst fines have a particle size less than 40 microns, based upon the total weight of the catalyst fines.

9. The process of claim 1, wherein about 80 wt. % or more of the catalyst fines have a particle size of about 20 microns or less, based upon the total weight of the catalyst fines.

10. The process of claim 1, wherein the step of (d) transporting occurs at a second velocity and the second velocity is from about 1 ft/sec (0.3 m/sec) to about 60 ft/sec (18 m/sec).

11. The process of claim 1, wherein the step of (d) transporting occurs at a second velocity and the second velocity is from about 1 ft/sec (0.3 m/sec) to about 40 ft/sec (12 m/sec).

12. The process of claim 1, wherein the step of (d) transporting occurs at a second velocity and the second velocity is from about 2 ft/sec 0.6 m/sec) to about 10 ft/sec (3 m/sec).

13. The process of claim 1, wherein the first conduit is in fluid communication with one or more heat exchangers, wherein the reactor effluent stream travels through the one or more heat exchangers at a third velocity of about 100 ft/sec (30 m/sec) or greater.

14. A process for recovering one or more olefin product(s) from an oxygenate-to-olefin reactor, the process comprising the steps of:
    (a) withdrawing a reactor effluent stream from the reactor, the reactor effluent stream having catalyst fines therein;
    (b) transporting the reactor effluent stream in a first conduit to a quench device at a first velocity of about 100 ft/sec (30 m/sec) or greater, wherein the first conduit has a conduit diameter and has one or more bends each having a bend radius, such that a ratio of the bend radius to the conduit diameter is about 1:1 or greater;
    (c) quenching the reactor effluent stream with a quench medium in a quench device to form a quenched effluent stream and a liquid fraction, the liquid fraction comprising a majority of the catalyst fines;
    (d) transporting the liquid fraction in a second conduit to a solids separation device, wherein the liquid fraction travels through the second conduit at a second velocity ranging from about 1 ft/sec (0.3 m/sec) to about 60 ft/sec (18 m/sec); and
    (e) recovering the one or more olefin product(s) from the quenched effluent stream.

15. The process of claim 14, wherein the quench medium has about 1 wt. % or less catalyst fines based upon the total weight of the quench medium.

16. The process of claim 14, wherein the quench device has a contact zone with structured packing.

17. The process of claim 14, wherein the first conduit has a conduit diameter and has one or more bends each having a bend radius, wherein a ratio of the bend radius to the conduit diameter is about 2.0:1.0 or greater.

18. The process of claim 14, wherein the reactor effluent stream has a dewpoint and the reactor effluent stream remains at a temperature above the dewpoint during the step (b) of transporting.

19. The process of claim 14, wherein the first velocity is from about 100 ft/sec (30 m/sec) to about 300 ft/sec (90 m/sec).

20. The process of claim 14, wherein the first velocity is from about 100 ft/sec (30 m/sec) to about 200 ft/sec (60 m/sec).

21. The process of claim 14, wherein about 95 wt. % or more of the catalyst fines have a particle size less than 40 microns, based upon the total weight of the catalyst fines.

22. The process of claim 14, wherein about 80 wt. % or more of the catalyst fines have a particle size less than 20 microns, based upon the total weight of the catalyst fines.

23. The process of claim 14, wherein the second velocity is 1 from about 1 ft/sec (0.3 m/sec) to about 40 ft/sec (12 m/sec).

24. The process of claim 14, wherein the second velocity is from about 2 ft/sec (0.6 m/sec) to about 10 ft/sec (3 m/sec).

25. The process of claim 14, wherein the first conduit is in fluid communication with one or more heat exchangers, wherein the reactor effluent stream travels through the one or more heat exchangers at a third velocity of about 100 ft/sec (30 m/sec) or greater.

26. A process for making one or more polymer product(s) from natural gas, the process comprising the steps of:
   (a) converting the natural gas to an oxygenate;
   (b) contacting the oxygenate with a molecular sieve catalyst in an oxygenate-to-olefin reactor;
   (c) withdrawing a reactor effluent stream from the oxygenate-to-olefin reactor, the reactor effluent stream comprising water and one or more olefin product(s) and having catalyst fines therein;
   (d) transporting the reactor effluent stream in a first conduit to a quench device, wherein the reactor effluent stream travels through the first conduit at a first velocity of about 100 ft/sec (30 m/sec) or greater, and wherein the first conduit has a conduit diameter and has one or more bends each having a bend radius, such that a ratio of the bend radius to the conduit diameter is about 1:1 or greater;
   (e) quenching the reactor effluent stream with a quench medium in a quench device to form a quenched effluent stream and a liquid fraction, the liquid fraction comprising the catalyst fines and water;
   (f) transporting the liquid fraction in a second conduit to a solids separation device, wherein the liquid fraction travels through the second conduit at a second velocity ranging from about 1 ft/sec (0.3 m/sec) to about 60 ft/sec (18 m/sec);
   (g) recovering the one or more olefin product(s) from the quenched effluent stream; and
   (h) polymerizing the one or more olefin product(s) to form the one or more polymer product(s).

27. The process of claim 26, wherein the quench medium has about 1 wt. % or less catalyst fines based upon the total weight of the quench medium.

28. The process of claim 26, wherein the quench device has a contact tone with structured packing.

29. The process of claim 26, wherein the first conduit has a conduit diameter and has one or more bends each having a bend radius, wherein a ratio of the bend radius to the conduit diameter is about 2.0:1.0 or greater.

30. The process of claim 26, wherein the reactor effluent stream has a dewpoint and the reactor effluent stream remains at a temperature above the dewpoint during the step (d) of transporting.

31. The process of claim 26, wherein about 95 wt. % or more of the catalyst fines have a particle size less than 40 microns, based upon the total weight of the catalyst fines.

32. The process of claim 26, wherein about 80 wt. % or more of the catalyst fines have a particle size of about 20 microns or less, based upon the total weight of the catalyst fines.

33. The process of claim 26, wherein the second velocity is from about 1 ft/sec (0.3 m/sec) to about 40 ft/sec (12 m/sec).

34. The process of claim 26, wherein the second velocity is from about 2 ft/sec (0.6 m/sec) to about 10 ft/sec (3 m/sec).

35. The process of claim 26, wherein the first conduit is in fluid communication with one or more heat exchangers, wherein the reactor effluent stream travels through the one or more heat exchangers at a third velocity of about 100 ft/sec (30 m/sec) or greater.

36. A process for recovering one or more olefin product(s) from a reactor effluent stream that is withdrawn from an oxygenate-to-olefin reactor, wherein the reactor effluent stream comprises olefins and water and contains catalyst fines, the process comprising the steps of:
   (a) transporting the reactor effluent stream in a first conduit to a quench device, wherein the reactor effluent stream travels through the first conduit at a first velocity of 100 ft/sec (30 m/sec) or greater, and wherein the first conduit has a conduit diameter and has one or more bends each having a bend radius, such that a ratio of the bend radius to the conduit diameter is about 1:1 or greater;
   (b) quenching the reactor effluent stream with a quench medium in a quench device to form a quenched effluent stream and a liquid fraction, the liquid fraction comprising the catalyst fines and the water;
   (c) transporting the liquid fraction in a second conduit to a solids separation device, wherein the liquid fraction travels through the second conduit at a second velocity ranging from about 1 ft/sec (0.3 m/sec) to about 60 ft/sec (1.8 m/sec); and
   (d) recovering the one or more olefin product from the quenched effluent stream.

37. The process of claim 36, wherein to quench medium has about 1 wt. % or less catalyst fines based upon the total weight of the quench medium.

38. The process of claim 36, wherein the quench device has a contact zone with structured packing.

39. The process of claim 36, wherein the first conduit has a conduit diameter and has one or more bends each having a bend radius, wherein a ratio of the bend radius to the conduit diameter is about 2.0:1.0 or greater.

40. The process of claim 36, wherein the reactor effluent stream has a dewpoint and the reactor effluent stream remains at a temperature above the dewpoint during the step (a) of transporting.

41. The process of claim 36, wherein the first velocity is from about 100 ft/sec (30 m/sec) to about 300 ft/sec (90 m/sec).

42. The process of claim 36, wherein the first velocity is from about 100 ft/sec (30 m/sec) to about 300 ft/sec (90 m/sec).

43. The process of claim 36, wherein about 90 wt. % or more of the catalyst fines have a particle size less than 40 microns, based upon the total weight of the catalyst fines.

44. The process of claim 36, wherein about 80 wt. % or more of the catalyst fines have a particle size of about 20 microns, based upon the total weight of the catalyst fines.

45. The process of claim 36, wherein the second velocity is from about 2 ft/sec (0.6 m/sec) to about 10 ft/sec (3 m/sec).

46. The process of claim 36, wherein the second velocity is from about 6 ft/sec (1.8 m/sec) to about 8 ft/sec (2.4 m/sec).

47. The process of claim 36, wherein the first conduit is in fluid communication with one or more heat exchangers, wherein the reactor effluent stream travels through the one or more heat exchangers at a third velocity of about 40 ft/sec (12 m/sec) or greater.

48. The process of claim 36, wherein the catalyst fines are silicoaluminophosphate molecular sieve catalyst fines.

49. The process of claim 1, wherein the first conduit has a first starting capacity and a first one-year capacity, the second conduit has a second starting capacity and a second one-year capacity, and the third conduit has a third starting capacity and a third one-year capacity, and wherein at least one of the first, second, and third one-year capacities are within 95 vol % of the first, second, and third starting capacities, respectively.

50. The process of claim 14, wherein the first conduit has a first starting capacity and a first one-year capacity, the second conduit has a second starting capacity and a second one-year capacity, and the third conduit has a third starting capacity and a third one-year capacity, and wherein at least one of the first, second, and third one-year capacities are within 95 vol % of the first, second, and third starting capacities, respectively.

51. The process of claim 26, wherein the first conduit has a first starting capacity and a first one-year capacity, the second conduit has a second starting capacity and a second one-year capacity, and the third conduit has a third staring capacity and a third one-year capacity, and wherein at least one of the first, second, and third one-year capacities are within 95 vol % of the first, second, and third starting capacities, respectively.

52. The process of claim 36, wherein the first conduit has a first starting capacity and a first one-year capacity, the second conduit has a second starting capacity and a second one-year capacity, and the third conduit has a third starting capacity and a third one-year capacity, and wherein at least one of the first, second, and third one-year capacities are within 95 vol % of the first, second, and third starting capacities, respectively.

* * * * *